United States Patent
Tseng

(10) Patent No.: US 6,187,203 B1
(45) Date of Patent: *Feb. 13, 2001

(54) SAMPLE PURIFICATION APPARATUS AND METHOD

(75) Inventor: Tsung-Che Tseng, Taipei (TW)

(73) Assignee: Academia Sinica, Taipei (TW)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/203,454

(22) Filed: Dec. 1, 1998

(51) Int. Cl.$^7$ .................................................. B01D 15/08
(52) U.S. Cl. .................... 210/656; 210/694; 210/198.2; 530/317; 530/417; 514/11
(58) Field of Search ..................... 210/635, 656, 210/660, 198.2, 694; 530/317, 412, 417, 422, 423, 427; 514/11

(56) References Cited

U.S. PATENT DOCUMENTS

| | | | |
|---|---|---|---|
| 3,697,581 | * 10/1972 | Humber | 260/479 R |
| 3,832,405 | * 8/1974 | Humber | 260/612 R |
| 3,843,727 | * 10/1974 | Humber | 260/570.7 |
| 4,049,653 | * 9/1977 | Winn | 544/150 |
| 4,744,981 | * 5/1988 | Pavanasasium | 424/85 |
| 4,895,808 | 1/1990 | Romer | 436/178 |
| 4,906,452 | * 3/1990 | Sivam | 424/10 |
| 4,996,277 | * 2/1991 | Bradshaw | 210/656 |
| 5,110,558 | 5/1992 | Romer | 422/101 |
| 5,373,008 | * 12/1994 | Gopalan | 514/227.8 |

OTHER PUBLICATIONS

Croteau et al., "Analysis of Trichothecene Mycotoxins by Gas Chromatography with Electron Capture Detection" J. Agric. Food Chem., 1994, 42:928–933.
Lauren et al., "Multitoxin Screening Method for Fusarium Mycotoxins in Grains", J. Agric. Food Chem., 1991, 39:502–507.
Romer, "Analytical Approaches to the Trichothecene Mycotoxins", Cereal Foods World, pp. 521–523, 1977.
Romer, "Use of Small Charcoal/Alumina Cleanup Columns in Determination of Trichothecene Mycotoxins in Foods and Feeds", J. Assoc. Off. Anal. Chem. 69(4):699–703, 1986.

* cited by examiner

Primary Examiner—Ernest G. Therkorn
(74) Attorney, Agent, or Firm—Fish & Richardson P.C.

(57) ABSTRACT

An apparatus for removing impurities from a liquid and a method for purifying a fusarium toxin in a solution extracted from an infected source is described. The method includes passing the solution through a layer of activated charcoal prior to a layer of aluminum oxide.

SAMPLE PURIFICATION APPARATUS AND METHOD

BACKGROUND OF THE INVENTION

This invention relates to an apparatus and method of purification of a fusarium toxin.

Fusarium fungi can infect cereal grains, e.g., corn and animal feeds, e.g., hay, to produce fusarium toxins. Fusarium toxins are carcinogenic and can cause digestive disorders or kidney failure. Therefore, it is important to identify such infected plants before their consumption by animals.

SUMMARY OF THE INVENTION

An aspect of the invention features an apparatus for removing impurities from a liquid. The apparatus, e.g., a column, includes an inlet and an outlet for introducing and removing the liquid, respectively. The inlet and the outlet are connected by a flow path. A flow path is the route by which a solvent travels through the apparatus. A layer of activated charcoal and a layer of aluminum oxide are disposed between the inlet and the outlet and in the flow path such that the layer of activated charcoal is closer to the inlet than the layer of aluminum oxide. In other words, the liquid introduced from the inlet flows through the layer of activated charcoal prior to flowing through the layer of aluminum oxide and exiting the outlet. Activated charcoal that has a particle size range of 100–400 mesh and aluminum oxide, e.g., neutral aluminum oxide, that has a particle size range of 70–230 mesh are examples of packing materials, e.g., stationary phase, that can be employed in this invention.

Another aspect of this invention features an apparatus which includes a container having an inlet and an outlet for introducing and removing the liquid, respectively. The inlet and the outlet are connected by a flow path. A layer of activated charcoal and a layer of aluminum oxide are disposed within an interior volume of the container and between the inlet and the outlet such that the liquid introduced from the inlet flows through the layer of activated charcoal prior to flowing through the layer of aluminum oxide and exiting the outlet.

In another aspect, the invention features a method of purifying a fusarium toxin in a solution. The solution can be extracted from an infected source, e.g., a plant. When the source comes from an animal, the toxin is a result of ingestion of fusarium toxin-containing plants. The method includes the steps of passing the solution having a fusarium toxin through an apparatus which contains a layer of activated charcoal and a layer of aluminum oxide such that the solution passes through the layer of activated charcoal prior to the layer of aluminum oxide. As described above, activated charcoal that has a particle size range of 100–400 mesh and aluminum oxide, e.g., neutral aluminum oxide, that has a particle size range of 70–230 mesh can be employed in this method. The fusarium toxin can be verrucarol, scirpentriol, diacetoxyscirpenol, T-2 tetrol, HT-2 toxin, T-2 toxin, iso-T-2 toxin, nivalenol, fusarenon-X, deoxynivalenol, 3-acetyl-DON, 15-acetyl-DON, 3,15-diacetyl-DON, 3-acetyl T-2 toxin, 15-acetyl T-2 toxin, 3-hydroxy HT-2 toxin, or dihydronivalenol. The fusarium toxin can be dissolved in an aqueous solution before passing through the activated charcoal and aluminum oxide layers. The aqueous solution can contain organic solvents, e.g., up to 90% (v/v). Some examples of organic solvents are acetonitrile, methanol, or chloroform.

A further aspect of the present invention features a method of purifying a fusarium toxin in a sample including the steps of introducing the sample into an inlet of an apparatus; passing the sample through a layer of activated charcoal within the apparatus; passing the sample through a layer of aluminum oxide within the apparatus; and finally, removing the sample through an outlet of the apparatus.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications mentioned herein are incorporated by reference in their entirety. In case of conflict, the present specification, including definitions, will control. In addition, the materials, methods, and examples are illustrative only and not intended to be limiting.

Other features or advantages of the present invention will be apparent from the following detailed description of several embodiments, and also from the appending claims.

DETAILED DESCRIPTION OF THE INVENTION

Figure 1:
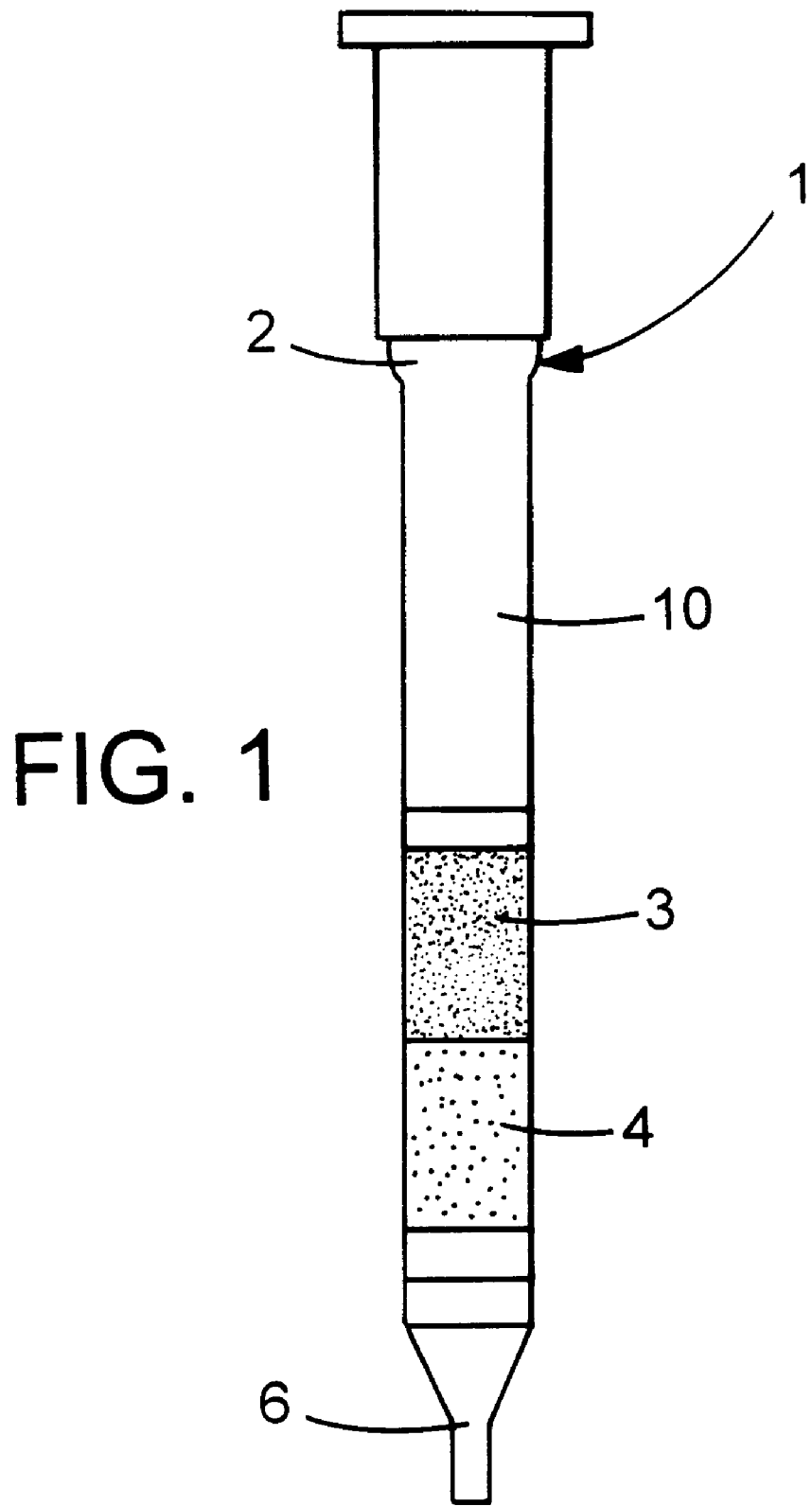
FIG. 1 depicts an apparatus containing a layer of activated charcoal and a layer of aluminum oxide.

The present invention features an apparatus and a method of removing impurities from a liquid containing an analyte, thereby facilitating the analysis of such an analyte in the liquid.

FIG. 1 depicts a chromatographic column 1. Column 1 contains inlet 2 for introducing a liquid sample to be purified and outlet 6 or allowing the purified liquid sample to exit. Inlet 2 and outlet 6 are connected by flow path 10 of the liquid sample.

Column 1 contains a layer of activated charcoal 3 and a layer of aluminum oxide 4 as a stationary phase between inlet 2 and outlet 6. It is important to pack the two layers such that the liquid sample flows through the layer of activated charcoal before the layer of aluminum oxide. In other words, the layer of activated charcoal should be deposited closer to the inlet than the layer of aluminum oxide. The order by which the liquid sample passes through these two layers enables the liquid sample to contact the activated charcoal layer first which has a larger capacity for removing impurities, e.g., pigments. The sample then passes through the aluminum oxide layer which serves to eliminate the remaining impurities, e.g., fats, carbohydrates, and proteins. Satisfactory results can be obtained with activated charcoal of the size 100–400 mesh and aluminum oxide of the size 70–230 mesh.

A layer of glass wool can be placed at each end of the stationary phase to filter out insoluble impurities and to keep the stationary phase packed tightly together. Optionally, a reservoir can be connected to inlet 2 for holding a large volume of solvent during the purification.

The above-described column can be used in removing impurities from a sample, e.g, a fusarium toxin-containing extract, thereby purifying the desired compound, e.g., fusarium toxin, in the sample. A fusarium toxin-containing extract can be obtained from a Fusarium fungi-infected plant sample, e.g., bean, corn, or oat, which are characterized by the presence of pale grey or pink coloration. The sample can be ground into a powder and extracted with an aqueous solution, e.g., a solution of water and acetonitrile, in a blender. The fusarium toxin can then be purified by passing the extract through a column as described above. Note that the impurity-removing process requires that the extract passes through the layer of activated charcoal prior to the layer of aluminum oxide. To facilitate the passing of the extract through the stationary phase, outlet 6 may be connected to an aspirator or a vacuum pump. The eluent collected can then be analyzed for fusarium toxins by techniques such as thin layer chromatography (TLC) and gas chromatography (GC).

The following specific example, which describes the set up of the column, the preparation and purification of the infected plant sample, and the analysis of the eluent, is to be construed as merely illustrative, and not limitative of the remainder of the disclosure in any way whatsoever.

EXAMPLE

Column Preparation

Glass wool was first placed directly above the outlet of a column (formed a layer of about 1 mm in height). The column was packed sequentially with 0.6 g of neutral alumina (70–230 mesh, Merck) and 0.2 g of activated charcoal (100–400 mesh, Sigma). The column was lightly tapped to ensure tight packing of the activated charcoal and alumina layers. Glass wool was then placed on top of the activated charcoal layer. The column was then sat on top of a suction flask which was connected to a vacuum pump. A rubber ring was placed in between the flask and the column to form an air-tight system.

Sample Preparation

Approximately 5 kg of beans (*Phaseolus vulgaris L.*) was harvested from a 0.5 hectare bean farm. The beans were stored at 4° C. before they were sorted into three types visually for analysis of fusarium toxin. They were: healthy beans without any apparent coloration ($S_1$), a mixture of beans with whitish grey or pink coloration ($S_2$), and beans with pink coloration ($S_3$). Note that Fusarium fungi infected beans have the characteristic coloration of whitish grey or pink.

Sample Extraction and Purification

For each type of beans collected, a 25 g finely powdered sample was mixed with a 100 mL aqueous solution of $CH_3CN$/water (8/2) to form a mixture. Extraction was performed by mixing the mixture in an Ultra Turrax T-25 blender (Janke & Kunkel Gmbh & Co., Germany) at 9,500 rpm for 3 minutes and filtering through a filter paper (Whatman No. 4). Approximately 8 mL of the filtrate was then passed through the charcoal- and alumina-containing column described above. For comparison, the same amount of filtrate was purified by a MycoSep™ #225 column (Romer, *J. Assoc. Off. Anal. Chem.*, 69(4):699–703 (1986)). All experiments were carried out in triplicate and data presented are the average of values. iv) Toxin identification Eluate collected from each of the two columns was analyzed by thin-layer chromatography (TLC) for the identification of diacetexyscirpenol (DAS), deoxynivalenol (DON), and T-2 toxin (T-2). Eluate samples were spotted on TLC plates (Aluminum silica gel 60, Merck) along with standards and developed in a solution of toluene/ethyl acetate/88% formic acid (6/2/1). The toxin spots were detected by using 20% $AlCl_3$ in methanol and comparing with the toxins present in the standards. Quantification of the toxins was done by gas chromatography (Hitachi model 163 equipped with flame ionization detector). See Scott et al., *J. Assoc. Off. Anal. Chem.* 69:889–893 (1986).

From the GC analysis, it was unexpectedly found that the amounts of each DAS, DON, and T-2 collected using the column of this invention were significantly more than those collected using the #225 column. For example, the amount of DAS collected using the column of this invention was about 4 times more than that collected using the #225 column. As another example, the amount of T-2 collected using the column of this invention was more than 7 times more than that collected using the #225 column. The experiment thus demonstrated that the column of this invention has a much higher efficiency than that of the #225 column.

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of purifying a fusarium toxin in a solution, comprising passing the solution through an apparatus having a layer of activated charcoal and a layer of aluminum oxide such that the solution passes through the layer of activated charcoal prior to the layer of aluminum oxide.

2. The method of claim 1, wherein the contaminated source originates from a plant.

3. The method of claim 1, wherein the fusarium toxin is verrucarol, scirpentriol, diacetoxyscirpenol, T-2 tetrol, HT-2 toxin, T-2 toxin, iso-T-2 toxin, nivalenol, fusarenon-X, deoxynivalenol, 3-acetyl-DON, 15-acetyl-DON, 3,15-diacetyl-DON, 3-acetyl T-2 toxin, 15-acetyl T-2 toxin, 3-hydroxy HT-2 toxin, or dihydronivalenol.

4. The method of claim 1, wherein the fusarium toxin is diacetoxyscirpenol, T-2 toxin, or deoxynivalenol.

5. The method of claim 1, wherein the fusarium toxin is dissolved in an aqueous solution.

6. The method of claim 5, wherein the aqueous solution contains acetonitrile, methanol, or chloroform.

7. The method of claim 5, wherein the aqueous solution contains acetonitrile. 14.

8. The method of claim 1, wherein the activated charcoal has a particle size rarge of 100 to 400 mesh.

9. The method of claim 8, wherein the aluminum oxide has a particle size range of 70 to 230 mesh.

10. The method of claim 9, wherein the fusarium toxin is dissolved in an aqueous solution.

11. The method of claim 10, wherein the aqueous solution contains acetonitrile.

12. The method of claim 1, wherein the aluminum oxide has a particle size range of 70 to 230 mesh.

13. The method of claim 1, wherein the aluminum oxide is neutral.

14. A method of purifying a fusarium toxin in a sample comprising:

introducing the sample into an inlet of an apparatus;

passing the sample through a layer of activated charcoal within the apparatus;

passing the sample through a layer of aluminum oxide within the apparatus; and removing the sample through an outlet of the apparatus.

* * * * *